(12) United States Patent
Scott et al.

(10) Patent No.: US 11,391,635 B2
(45) Date of Patent: Jul. 19, 2022

(54) PRESSURE ADAPTIVE SENSING SYSTEM AND METHOD

(71) Applicant: Tactual Labs Co., New York, NY (US)

(72) Inventors: Douglas Ainsworth Scott, Bracknell (GB); Valkyrie Savage, Toronto (CA); Maria Ruiz Maya, Austin, TX (US)

(73) Assignee: Tactual Labs Co., New York, NY (US)

( * ) Notice: Subject to any disclaimer, the term of this patent is extended or adjusted under 35 U.S.C. 154(b) by 81 days.

(21) Appl. No.: 16/909,764

(22) Filed: Jun. 23, 2020

(65) Prior Publication Data

US 2020/0408615 A1    Dec. 31, 2020

Related U.S. Application Data

(60) Provisional application No. 62/866,302, filed on Jun. 25, 2019.

(51) Int. Cl.
*G01L 1/04* (2006.01)
*G01L 1/02* (2006.01)

(52) U.S. Cl.
CPC . *G01L 1/04* (2013.01); *G01L 1/02* (2013.01)

(58) Field of Classification Search
CPC ....... A61B 5/0507; G06F 3/0416; G01L 1/04; G01L 1/02
USPC .................................................... 73/862.625
See application file for complete search history.

(56) References Cited

U.S. PATENT DOCUMENTS

| | | | |
|---|---|---|---|
| 9,775,763 B2* | 10/2017 | Aleksov | A61H 1/0266 |
| 9,877,659 B2* | 1/2018 | Lee | A61B 5/0004 |
| 9,907,473 B2* | 3/2018 | Tran | A61B 5/6802 |
| 2002/0026114 A1* | 2/2002 | Nissila | A61B 5/25 600/384 |
| 2006/0212097 A1* | 9/2006 | Varadan | A61B 5/076 607/62 |
| 2016/0058133 A1* | 3/2016 | Fournier | G06F 21/32 455/41.2 |

* cited by examiner

*Primary Examiner* — Octavia Hollington
(74) *Attorney, Agent, or Firm* — Adam Landa

(57) ABSTRACT

A pressure adaptive sensor system has at least one transmitting antenna and at least one receiving antenna adapted to receive a signal from at least one transmitting antenna. A measurement of received signals is used in order to determine pressure of an operable portion of the electrode on an object. The determined pressure is used by a pressure actuator to alter a contact profile when an electrode is in contact with skin or a surface.

9 Claims, 9 Drawing Sheets

PRESSURE ADAPTIVE SENSING SYSTEM AND METHOD

This application claims the benefit of U.S. Provisional Application No. 62/866,302 filed Jun. 25, 2019, the contents of which are incorporated herein by reference. This application includes material which is subject to copyright protection. The copyright owner has no objection to the facsimile reproduction by anyone of the patent disclosure, as it appears in the Patent and Trademark Office files or records, but otherwise reserves all copyright rights whatsoever.

FIELD

The disclosed apparatus and method relate to the field of sensors, in particular the disclosed apparatus and method relate to gesture and human interaction sensors and their application.

BRIEF DESCRIPTION OF THE DRAWINGS

The foregoing and other objects, features, and advantages of the disclosure will be apparent from the following more particular description of embodiments as illustrated in the accompanying drawings in which reference characters refer to the same parts throughout the various views. The drawings are not necessarily to scale, emphasis instead being placed upon illustrating principles of the disclosed embodiments.

DETAILED DESCRIPTION

Figure 1:
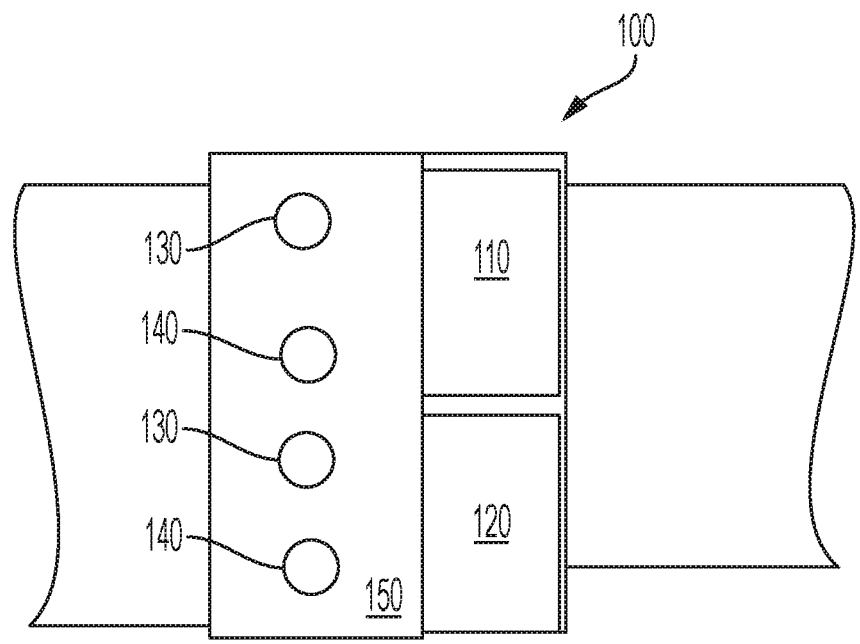
FIG. 1 shows a simplified diagram of a sensing system.

The application employs principles used in fast multi-touch sensors and other interfaces disclosed in the following: U.S. Pat. Nos. 9,933,880; 9,019,224; 9,529,476; 9,811,214; 9,804,721; 9,710,113; and 9,158,411. Familiarity with the disclosure, concepts and nomenclature within these patents is presumed. The entire disclosures of those patents and the applications incorporated therein by reference are incorporated herein by reference. This application also employs principles used in fast multi-touch sensors and other interfaces disclosed in the following: U.S. patent application Ser. Nos. 15/162,240; 15/690,234; 15/195,675; 15/200,642; 15/821,677; 15/904,953; 15/905,465; 15/943,221; 62/540,458, 62/575,005, 62/621,117, 62/619,656 and PCT publication PCT/US2017/050547, familiarity with the disclosures, concepts and nomenclature therein is presumed. The entire disclosure of those applications and the applications incorporated therein by reference are incorporated herein by reference.

As used herein, and especially within the claims, ordinal terms such as first and second are not intended, in and of themselves, to imply sequence, time or uniqueness, but rather, are used to distinguish one claimed construct from another. In some uses where the context dictates, these terms may imply that the first and second are unique. For example, where an event occurs at a first time, and another event occurs at a second time, there is no intended implication that the first time occurs before the second time, after the second time or simultaneously with the second time. However, where the further limitation that the second time is after the first time is presented in the claim, the context would require reading the first time and the second time to be unique times. Similarly, where the context so dictates or permits, ordinal terms are intended to be broadly construed so that the two identified claim constructs can be of the same characteristic or of different characteristics. Thus, for example, a first and a second frequency, absent further limitation, could be the same frequency, e.g., the first frequency being 10 Mhz and the second frequency being 10 Mhz; or could be different frequencies, e.g., the first frequency being 10 Mhz and the second frequency being 11 Mhz. Context may dictate otherwise, for example, where a first and a second frequency are further limited to being frequency orthogonal to each other, in which case, they could not be the same frequency.

Certain principles of a fast multi-touch (FMT) sensor have been disclosed in the patent applications discussed above. Orthogonal signals may be transmitted into a plurality of transmitting antennas (or conductors) and information may be received by receivers attached to a plurality of receiving antennas (or conductors). In an embodiment, receivers "sample" the signal present on the receiving antennas (or conductors) during a sampling period ($\tau$). In an embodiment, signal (e.g., the sampled signal) is then analyzed by a signal processor to identify touch events (including, e.g., actual touch, near touch, hover and farther away events that cause a change in coupling between a transmitting antenna (or conductor) and receiving antennas (or conductor)). In an embodiment, one or more transmitting antennas (or conductors) can move with respect to one or more receiving antennas (or conductors), and such movement causes a change of coupling between at least one of the transmitting antennas (or conductors) and at least one of the receiving antennas (or conductors). In an embodiment, one or more transmitting antennas (or conductors) are relatively fixed with respect to one or more receiving antennas (or conductors), and the interaction of the signal and/or signals transmitted with environmental factors causes a change of coupling between at least one of the transmitting antennas (or conductors) and at least one of the receiving antennas (or conductors). The transmitting antennas (or conductors) and receiving antennas (or conductors) may be organized in a variety of configurations, including, e.g., a matrix where the crossing points form nodes, and interactions are detected by processing of received signals. In an embodiment where the orthogonal signals are frequency orthogonal, spacing between the orthogonal frequencies, $\Delta f$, is at least the reciprocal of the measurement period $\tau$, the measurement period $\tau$ being equal to the period during which the column conductors are sampled. Thus, in an embodiment, the received at a column conductor may be measured for one millisecond ($\tau$) using frequency spacing ($\Delta f$) of one kilohertz (i.e., $\Delta f = 1/\tau$).

In an embodiment, the signal processor of a mixed signal integrated circuit (or a downstream component or software) is adapted to determine at least one value representing each frequency orthogonal signal transmitted to (or present on) a row conductor (or antenna). In an embodiment, the signal processor of the mixed signal integrated circuit (or a downstream component or software) performs a Fourier transform on the signals present on a receive antenna (or conductor). In an embodiment, the mixed signal integrated circuit is adapted to digitize received signals. In an embodiment, the mixed signal integrated circuit (or a downstream component or software) is adapted to digitize the signals present on the receive conductor or antenna and perform a discrete Fourier transform (DFT) on the digitized information. In an embodiment, the mixed signal integrated circuit (or a downstream component or software) is adapted to digitize the signals present on the received conductor or antenna and perform a Fast Fourier transform (FFT) on the digitized information—an FFT being one type of discrete Fourier transform.

It will be apparent to a person of skill in the art in view of this disclosure that a DFT, in essence, treats the sequence of digital samples (e.g., window) taken during a sampling period (e.g., integration period) as though it repeats. As a consequence, signals that are not center frequencies (i.e., not integer multiples of the reciprocal of the integration period (which reciprocal defines the minimum frequency spacing)), may have relatively nominal, but unintended consequence of contributing small values into other DFT bins. Thus, it will also be apparent to a person of skill in the art in view of this disclosure that the term orthogonal as used herein is not "violated" by such small contributions. In other words, as the term frequency orthogonal is used herein, two signals are considered frequency orthogonal if substantially all of the contribution of one signal to the DFT bins is made to different DFT bins than substantially all of the contribution of the other signal.

When sampling, in an embodiment, received signals are sampled at at least 1 MHz. In an embodiment, received signals are sampled at at least 2 MHz. In an embodiment, received signals are sampled at at least 4 Mhz. In an embodiment, received signals are sampled at 4.096 Mhz. In an embodiment, received signals are sampled at more than 4 MHz. To achieve kHz sampling, for example, 4096 samples may be taken at 4.096 MHz. In such an embodiment, the integration period is 1 millisecond, which per the constraint that the frequency spacing should be greater than or equal to the reciprocal of the integration period provides a minimum frequency spacing of 1 KHz. (It will be apparent to one of skill in the art in view of this disclosure that taking 4096 samples at e.g., 4 MHz would yield an integration period slightly longer than a millisecond, and not achieving kHz sampling, and a minimum frequency spacing of 976.5625 Hz.) In an embodiment, the frequency spacing is equal to the reciprocal of the integration period. In such an embodiment, the maximum frequency of a frequency-orthogonal signal range should be less than 2 MHz. In such an embodiment, the practical maximum frequency of a frequency-orthogonal signal range should be less than about 40% of the sampling rate, or about 1.6 MHz. In an embodiment, a DFT (which could be an FFT) is used to transform the digitized received signals into bins of information, each reflecting the frequency of a frequency-orthogonal signal transmitted which may have been transmitted by the transmitting antenna. In an embodiment 2048 bins correspond to frequencies from 1 KHz to about 2 MHz. It will be apparent to a person of skill in the art in view of this disclosure that these examples are simply that, exemplary. Depending on the needs of a system, and subject to the constraints described above, the sample rate may be increased or decreased, the integration period may be adjusted, the frequency range may be adjusted, etc.

In an embodiment, a DFT (which can be an FFT) output comprises a bin for each frequency-orthogonal signal that is transmitted. In an embodiment, each DFT (which can be an FFT) bin comprises an in-phase (I) and quadrature (Q) component. In an embodiment, the sum of the squares of the I and Q components is used as a measure corresponding to signal strength for that bin. In an embodiment, the square root of the sum of the squares of the I and Q components is used as measure corresponding to signal strength for that bin. It will be apparent to a person of skill in the art in view of this disclosure that a measure corresponding to the signal strength for a bin could be used as a measure related to muscle activity. In other words, the measure corresponding to signal strength in a given bin would change as a result of some activity originated by muscles of the body.

The sensing apparatuses discussed herein use transmitting and receiving antennas (also referred to herein as conductors, row conductors, column conductors, transmitting conductors, or receiving conductors). However, it should be understood that whether the transmitting antennas or receiving antennas are functioning as a transmitter, a receiver, or both depends on context and the embodiment. In an embodiment, the transmitters and receivers for all or any combination of the arrangements are operatively connected to a single integrated circuit capable of transmitting and receiving the required signals. In an embodiment, the transmitters and receivers are each operatively connected to a different integrated circuit capable of transmitting and receiving the required signals, respectively. In an embodiment, the transmitters and receivers for all or any combination of the patterns may be operatively connected to a group of integrated circuits, each capable of transmitting and receiving the required signals, and together sharing information necessary to such multiple IC configuration. In an embodiment, where the capacity of the integrated circuit (i.e., the number of transmit and receive channels) and the requirements of the patterns (i.e., the number of transmit and receive channels) permit, all of the transmitters and receivers for all of the multiple patterns used by a controller are operated by a common integrated circuit, or by a group of integrated circuits that have communications therebetween. In an embodiment, where the number of transmit or receive channels requires the use of multiple integrated circuits, the information from each circuit is combined in a separate system. In an embodiment, the separate system comprises a GPU and software for signal processing.

In an embodiment, the mixed signal integrated circuit is adapted to generate one or more signals and send the signals to the transmitting antennas via the transmitter. In an embodiment, the mixed signal integrated circuit is adapted to generate a plurality of frequency orthogonal signals and send the plurality of frequency orthogonal signals to the transmitting antennas. In an embodiment, the mixed signal integrated circuit is adapted to generate a plurality of frequency orthogonal signals and one or more of the plurality of frequency orthogonal signals to each of a plurality of transmit antennas. In an embodiment, the frequency orthogonal signals are in the range from DC up to about 2.5 GHz. In an embodiment, the frequency orthogonal signals are in the range from DC up to about 1.6 MHz. In an embodiment, the frequency orthogonal signals are in the range from 50 KHz to 200 KHz. The frequency spacing between the frequency orthogonal signals should be greater than or equal to the reciprocal of the integration period (i.e., the sampling period).

In an embodiment, the mixed signal integrated circuit (or a downstream component or software) is adapted to determine at least one value representing each frequency orthogonal signal transmitted by a transmitting antenna. In an embodiment, the mixed signal integrated circuit (or a downstream component or software) performs a Fourier transform to received signals. In an embodiment, the mixed signal integrated circuit is adapted to digitize received signals. In an embodiment, the mixed signal integrated circuit (or a downstream component or software) is adapted to digitize received signals and perform a discrete Fourier transform (DFT) on the digitized information. In an embodiment, the mixed signal integrated circuit (or a downstream component or software) is adapted to digitize received signals and perform a Fast Fourier transform (FFT) on the digitized information.

Turning to FIG. 1, a simplified diagram is shown that sets forth an example of a sensor system 100, which is incorporated into wearable 150. In FIG. 1, the wearable 150 is placed on a wrist. In an embodiment, a mixed signal integrated circuit with signal processing capabilities comprises a transmitter 110, and a receiver 120. In an embodiment, an analog front end comprising a transmitter (or multiple transmitters) and a receiver (or multiple receivers) is used to send and receive signals instead of the mixed signal integrated circuit. In such an embodiment, the analog front end provides a digital interface to signal generating and signal processing circuits and/or software. In an embodiment, the mixed signal integrated circuit is adapted to generate one or more signals and send the signals to the transmitting antenna 130 (also referred to as an electrode or conductor) via the transmitter 110. In an embodiment, the mixed signal integrated circuit 100 is adapted to generate a plurality of frequency-orthogonal signals and send the plurality of frequency-orthogonal signals to the transmitting antennas 130.

The transmitter 110 is conductively coupled to transmitting antennas 130, and the receiver 120 is operably connected to receiving antennas 140 (also referred to herein as conductors or electrodes). The transmitting antenna 130 is supported on the wearable 150 that is worn on a body part. It will be apparent to a person of skill in the art in view of this disclosure that the transmitting antennas and receiving antennas are arbitrarily assigned, and the transmitting antenna 130 can be used on the receive side, while the receiving antenna 140 can be used as the transmit side. It will also be apparent to a person of skill in the art in view of this disclosure that signal processor, transmitter and receiver may be implemented on separate circuits. It will be apparent to a person of skill in the art in view of this disclosure that the transmitter and receivers may support more than one antenna. In an embodiment, a plurality of transmitting antennas 130 and/or a plurality of receiving antennas 140 are employed.

Further discussion regarding the implementation of the transmitting antennas (or conductors) and receiving antennas (or conductors) in association with wearables can be found in U.S. patent application Ser. No. 15/926,478, U.S. patent application Ser. No. 15/904,953, U.S. patent application Ser. No. 16/383,090 and U.S. patent application Ser. No. 16/383,996, the contents of all of the aforementioned applications incorporated herein by reference.

While the embodiments discussed above and variations thereof are able to distinguish and determine position and movement, being able to establish the appropriate amount of contact a wearable has with a user can be important for establishing an engagement that provides good results. For example, establishing the presence of each transmitting antenna and receiving antenna can be significant when transmitting signals into a user's skin using infusion. The contact profile of the sensing system establishes the pressure with which the antennas are applied to the user's skin and the area that it contacts. The pressure with which the antennas are applied to the user's skin impacts the capabilities of the sensing system.

The contact profile of the sensing system transducer is established and maintained such that its operating characteristics and performance is optimally maintained. By maintaining the contact profile, disturbances caused when the body moves and deforms its shape during the taking of measurements are compensated for by the sensing. Additionally, changes in the physical characteristics of the body itself may change due to sweat, environmental humidity, temperature, respiration, or other effects.

The placement of electrodes (conductors or antennas) can be actively controlled through various mechanical and electronic actuation means. These movements can be both coarse and fine in order to reestablish a preferred contact profile. Maintaining the contact profile also aids in simplifying the calibration and data rectification process inherent in measurement systems which do not actively adapt the sensor. In an embodiment, a shape-changing soft electrode that can adjust the pressure applied to a surface is implemented. The curvature of the skin is complex and features hills and valleys of varying dimension, in an embodiment, the electrodes themselves are adapted to change their surface area or profile in order to better fit with and maintain pressure with a given portion of the skin.

Figure 2:
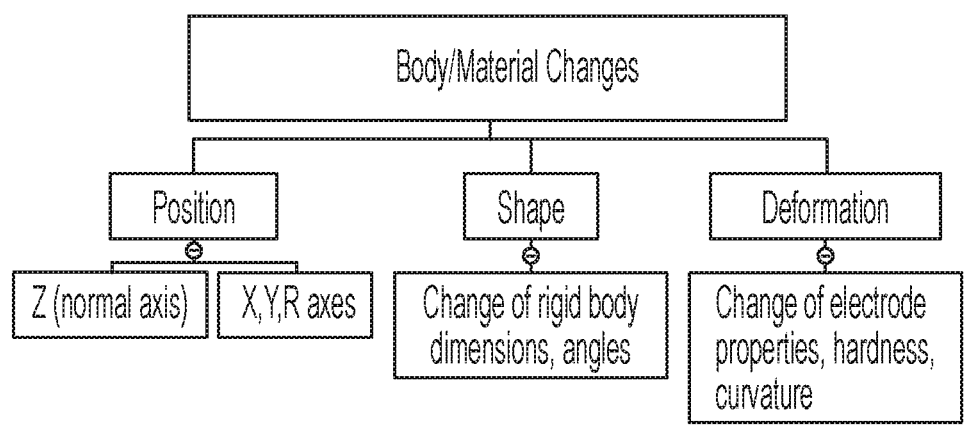
FIG. 2 shows a diagram illustrating potential changes that can impact the sensing system.

Referring to FIG. 2, shown is a diagram illustrating potential changes that can impact the sensing system. The change in position of the skin and or material on which the sensing system is placed is typically in the direction of the Z-axis, which is defined as the vector normal to the surface plane of the skin or material. Movement may also include movement along any combination of axes, such as the X, Y and/or R (radial) direction. As discussed above, the shape of the skin against a given sensor system interface area may change. For example, an electrode may be placed directly over a muscle, therefore, in an embodiment, the system includes mechanically adapting the sensor system shape to compensate. The adaptation is such that it will modify the amount of area that is contacted by the electrodes of the sensor system. In an embodiment, mechanical means are used in order to establish a contact profile with an individual. In an embodiment, a shape-changing electrode made of a conductive fabric wrapped around a smaller expanding bladder is able to change the amount of contact area that the electrode is providing with respect to skin.

The deformation of the skin against the surface of an electrode may change, for example, when an electrode is placed directly over a bone or tendon the movement of the bone or tendon may change the contact with the electrode. To compensate the sensor system includes mechanically deforming the surface of the electrode to compensate for changes in the electrode's contact profile. This can occur by typically adjusting the curvature, hardness and mold of an electrode so as to better conform to the skin/material deformation.

The skin surface and subdermal structures of the skin may further change properties. For example, surface resistance through processes like sweat and accumulated environmental humidity can impact the sensing profile of the sensing system. Therefore, in an embodiment, the system includes electronically adjusting the properties of the electrode to compensate for the changes in the surface resistance. For example, reducing current to the electrode when skin surface resistance is reduced, or adjusting AC frequency to achieve signal penetration through varying types and densities of tissue.

When employing the pressure adaptive sensor, a nominal operating characteristic is desired for the sensor system and is provided to a controller as a setpoint of a single or a combination of state variables. In an embodiment, the contact profile is obtained via an electrical impedance measurement. In an embodiment, the contact profile is obtained via electronic impedance tomography (EIT).

EIT provides a measure of the impedance path between skin and an electrode. A typical setpoint for the contact profile would therefore be a nominal real resistance and a complex reactance pair of variables. Additionally, other state variables may be specified inputs to the system. For example, physical actuator pressure on the electrode, which can be obtained either as direct feedback from a mechanical strain sensor or indirect feedback from an actuator drive power (voltage and current coupled) can be used in order to provide an indication of the pressure in the system and to obtain a contact profile for the electrodes with the surface of the skin.

Figure 3:
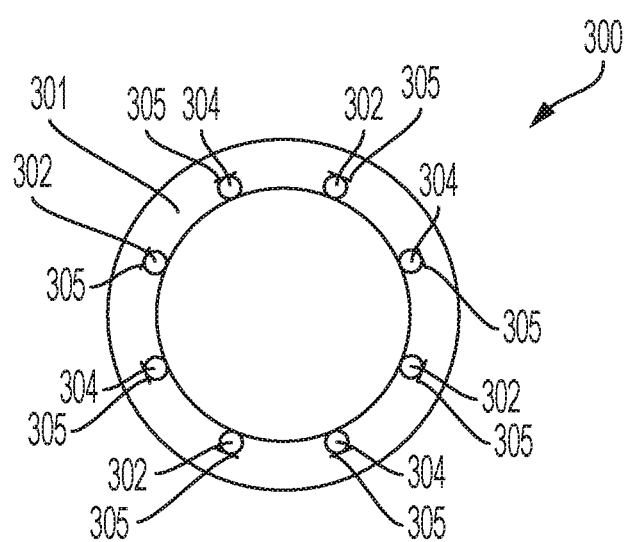
FIG. 3 is a diagram of a pressure adaptive sensing system.

Turning to FIG. 3, shown is an embodiment of a pressure adaptive sensor system 300 that implements a way in which the contact pressure of the transmitting electrodes 302 and/or receiving electrodes 304 on the skin can be established and adapted so as to maintain a preferred contact profile for the sensing system. The pressure adaptive sensor system 300 described herein may be used in order to complement additional sensing systems. For example the pressure adaptive sensor system 300 may be used in order to complement the sensing system 100 discussed above with respect to FIG. 1. The transmitting electrodes 302 (sometimes referred to as antennas or conductors) are adapted to be proximate to a user's skin when the wearable is being worn. The pressure adaptive sensor system 300 is able to ascertain the amount of contact between the transmitting electrodes 302 and the user's skin based on the measurements of signals received by the receiving electrodes 304.

In an embodiment, the sensor system is able to ascertain the amount of contact based on the impedance measurements of signals received through the skin. When impedance measurements change the information regarding the change in impedance can be used to determine how much contact the transmitting antennas have with the user's skin. In an embodiment, the sensing system is able to ascertain the amount of contact based on voltage measurements of signals received through the skin. When voltage measurements change, the information regarding the change in voltage can be used to determine how much contact the transmitting electrodes have with the user's skin. In an embodiment, the amount of contact is determined by directly determining the amount of pressure each transmitting electrode is imparting to the surface of the skin by using a physical actuator adapted to determine pressure. In an embodiment, the pressure that each transmitting electrode is imparting to the surface of the skin may be determined based on a plurality of measurements provided by separate sensors that are adapted to determine pressure based on physical contact.

Returning to FIG. 3, the transmitting electrodes 302 and the receiving electrodes 304 are placed on a substrate 301 that is formed as a wearable adapted to be placed on a wrist. In an embodiment, the wearable is a wristband. In an embodiment, the wearable is a bracelet. In an embodiment, the wearable is a glove/wristband combination. Signals received by the receiving electrodes 304 that are received from the transmitting electrodes 302 are used to establish measurements of impedance. The measurements of impedance are then processed and used in order to determine the amount of contact that each of the transmitting electrodes 302 have with the user's skin. The measurements are used to establish a profile of the location and placement of the transmitting electrodes 302.

Once the contact profile is established, the pressure adaptive sensor system 300 can further determine if this is the optimal contact profile needed in order to obtain all of the sensing modalities desired. For example, measurements of signals received at the receiving electrodes 304 may be used in order to obtain interior sensing of movement within the wrist area. The sensing of movement within the wrist area may be best obtained when the transmitting electrodes 302 and/or the receiving electrodes 304 are pressed at preferred pressure against the user's skin. In an embodiment, the optimal contact profile may a predetermined contact profile established by the known qualities of the preferred measurements. In an embodiment, the optimal contact profile may be a predetermined baseline profile established during initial set-up of the pressure adaptive sensor system 300. In an embodiment, the sensor system establishes a predetermined contact profile by taking into account characteristics of the user's skin, such as density, thickness, etc. In an embodiment, the predetermined contact profile takes into account the physical changes to a user's skin based on activity. In an embodiment, the optimal contact profile is itself adaptive and takes into account past uses of the pressure adaptive sensor system 300 in order to determine what the optimal contact profile should be. In an embodiment, the predetermined contact profile is a profile that establishes uniform contact of the transmitting electrodes 302 when worn. In an embodiment, the predetermined contact profile is a profile that establishes uniform contact of the receiving electrodes 304 when worn. In an embodiment, the predetermined contact profile is a profile that establishes uniform contact of the transmitting electrodes 302 and the receiving electrodes 304 when worn. In an embodiment, the predetermined contact profile is a profile that establishes uniform contact of a subset of the transmitting electrodes 302 or the receiving electrodes 304 based on the key points of location when being worn.

Still referring to FIG. 3, located on the substrate 301 is pressure actuator 305. The pressure actuator 305 is one of a plurality of pressure actuators 305. The pressure actuator 305 is operably connected to the processor (not shown) of the pressure adaptive sensor system 300. The pressure actuator 305 receives commands in response to the measurements made that establish the current profile and the changes necessary in order to obtain the optimal profile. The pressure actuator 305 then actuates so as to place the pressure adaptive sensor system 300 into an arrangement that substantially approaches or obtains the predetermined profile.

In an embodiment, the pressure actuator 305 is formed from a material that is adapted to change its physical properties based on the provision of signals. In an embodiment, the pressure actuator 305 is able to stiffen based on the provision of signals. The stiffening of the pressure actuator 305 will cause the transmitting electrodes 302 and/or receiving electrodes 304 to be moved into contact with a user's skin so as to meet the predetermined profile. For example, the pressure actuator 305 may be a muscle wire, such as Nitinol®, which is a nickel titanium alloy that is superelastic and retains shape memory. When an electric signal is applied to the Nitinol wires, the wires stiffens. This stiffening can be controlled so as to apply a specific amount of pressure and adjust contact profile accordingly. In an embodiment the pressure actuator is a hydraulic system that transmits fluid to specific locations on the substrate. The fluid may be water, fluids of varying viscosities, magnetic fluids, etc. When using a hydraulic system, the flow of water stiffens the portions of the substrate or wearable and is able to change the contact profile. In an embodiment, the pressure actuator is a pneumatic system that changes the flow of a gas located within the substrate. Changing the flow of gas is used to alter the contact profile. In an embodiment, the pressure actuator is a mechanical subsystem that employs physical movement via levers, etc. in order to alter the contact profile. In an embodiment, the pressure actuator is a magnetic actuator used to alter the contact profile.

Still referring to FIG. 3, the pressure actuators 305 are placed proximate to the transmitting electrodes 302 and receiving electrodes 304. The pressure actuators 305 are adapted to change the contact profile of the pressure adaptive sensor system 300 when actuated. In an embodiment, the pressure actuators are dispersed throughout the substrate. In an embodiment, the pressure actuators form a layer of material that has portions that are selectively activated.

When implemented in a wearable, the pressure adaptive sensing system 300 is able to actively adjust the contact profile of the wearable. This permits the sensing system employed in the wearable to obtain accurate measurements of the signals that they wish to receive. For example, in addition to the transmitting antennas discussed above that transmit signals into a user's skin, there may be additional transmitting antennas that are adapted to transmit a plurality of frequency orthogonal signals, such as discussed with respect to FIG. 1, and use those signals in order to determine movement and position of fingers and hands.

Turning to other ways in which pressure adaptation can be performed, when using an electrically controlled muscle wire, such as the Nickel Titanium Alloy, Nitinol®, for an actuator, electricity is applied to the wire and the wire mechanically shrinks in length. The wire shrinks only by a small amount, for example, the wire may shrink by 1-10% of its length. In an embodiment, the wire may shrink by 1-20% of its length. In an embodiment, the wire may shrink by 1-30% of its length.

In an embodiment, a longer effective length of wire is used by using the full length of a wearable and multiple cascaded segments of wire, either directly bonded, or attached via a pulley mechanism. The net effect is to achieve a larger linear movement of a swing arm, such that a transmitting (or receiving) electrode can swing through a full position range. A combination of mechanical pin-slot guides and springs is used to ensure the motion constraints on the electrode. In an embodiment, the muscle wire is electronically controlled by a programmable voltage/current drive circuit. In an embodiment DC complex control signals are used. In an embodiment, complex control signals are used. in an embodiment, PWM (pulse width modulation) signals are used. In an embodiment, hysteresis controller (i.e., "bang-bang") control methods are used. Such types of control signals are used in non-linear actuation.

In an embodiment, a spring is loaded so as to provide a biased force into the skin/material with which it makes contact. In an embodiment, muscle wire is used, the wire constricts which raises a spring that is providing the biased load. This type of arrangement balances the natural forces between skin contact pressure and the electrodes, with the muscle wire acting as a lower-power arbiter of net force.

Figure 4:
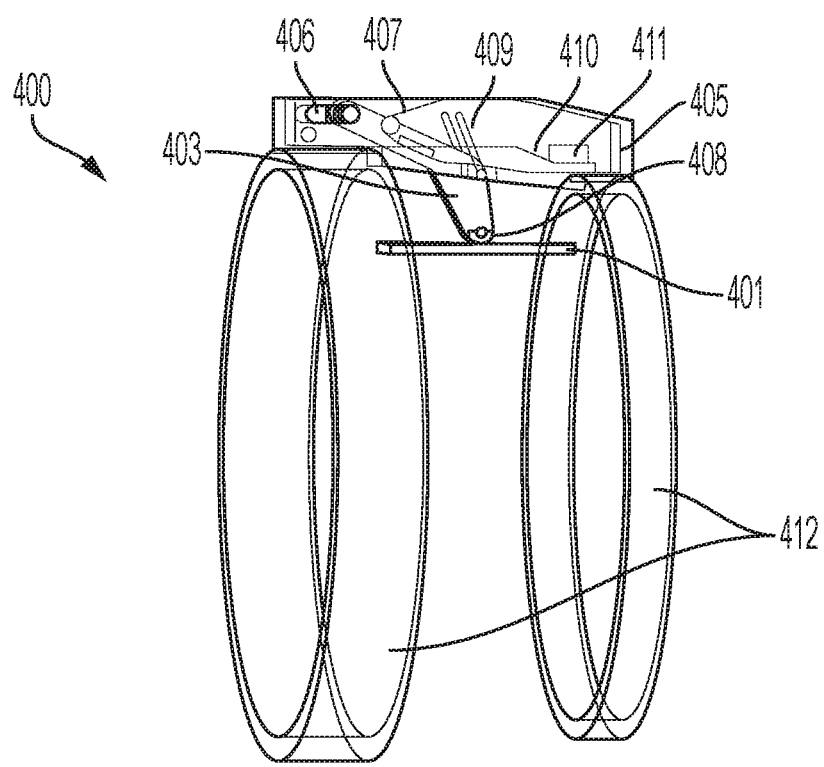
FIG. 4 is a diagram of a pressure adaptive sensing system.

Now referring to FIG. 4, shown is an actuator 405 for a sensing system 400. The actuator 405 comprises a torsion spring 407 and muscle wire 410. The electrode 401 (which can either be a transmitting or receiving electrode) is operably connected to a lever arm 403 through a hinge joint 408.

The hinge joint 408 permits uniaxial movement of the electrode 401. The lever arm 403 is movably supported via horizontal slot 406 and vertical slot 409. The horizontal slot 406 and the vertical slot 409 allows the lever arm 403 to move either in the horizontal or vertical direction. Variations of the arrangement of the horizontal slot 406 and the vertical slot 409 impacts the movement of the lever arm 403. It should be understood by one of skill in the art, in view of this disclosure, that arrangements of slots can be varied and assume a variety of angles and orientations depending upon the desired movement.

As discussed above, in addition to angles and orientations, in an embodiment, a shape-changing soft electrode that can adjust the pressure applied to a surface is implemented. The curvature of the skin is complex and features hills and valleys of varying dimension, in an embodiment, the electrodes themselves are adapted to change their surface area or profile in order to better fit with and maintain pressure with a given portion of the skin.

The muscle wire 410 is routed along the housing of the actuator 405 and connected to one of the sides of the lever arm 403. As current is applied to the muscle wire 410, the muscle wire 410 contracts and pulls the lever arm 403. The muscle wire 410 loops through cylindrical support 411. The torsion spring 407 exerts force on the lever arm 403 proportional to its angle of twist. This force exerted by the torsion spring 407 promotes contact between the electrode 401 and skin. Cuffs 412 are adapted to support the actuator 405 when worn on a body part, such as a wrist. It should be understood that if applied and used on other body parts, different accessories other than cuffs may be used.

An actuator similar to actuator 405 may be secured to other areas beside the wrist area. When secured to areas other than the wrist different arrangements, other than cuffs, may be used in order to secure the actuator portion to that area. In an embodiment, an actuator is secured to a leg. In an embodiment, an actuator 405 is secured to an arm. In an embodiment, an actuator 405 is secured to a neck. In an embodiment, an actuator 405 is secured to a waist. In an embodiment, an actuator 405 is secured to a head. In an embodiment, an actuator 405 is secured to a chest.

Figure 5:
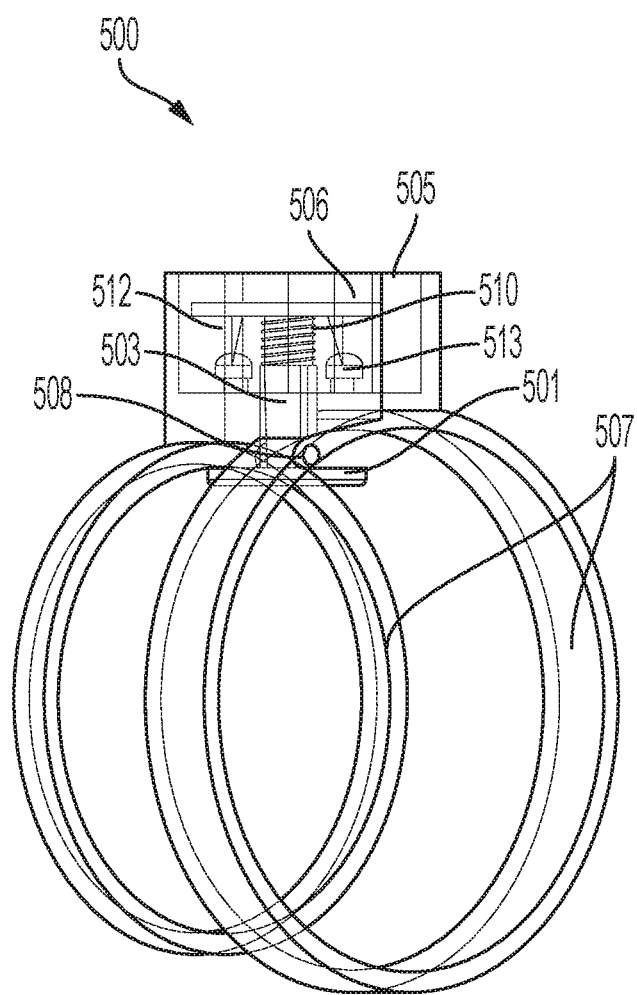
FIG. 5 is a diagram of a pressure adaptive sensing system.

Now referring to FIG. 5, shown is an embodiment of an actuator 505 for the sensing system 500 that uses a loaded spring 510. The loaded spring 510 surrounds a piston 503 that connects to the electrode 501. The top of the piston 503 is a portion 506 that is pulled via two o-rings 512 located on the sides of the piston 503 that are operably connected via hooks 513 to the o-rings 512. The loaded spring 506 provides a constant pressure that is applied in the direction of placing the electrode 501 on the surface of the skin. When a wearable is placed on a wrist (or other body part) and the electrode 501 makes contact with skin, pushing perpendicularly onto the piston 503 and the portion 506 of the piston 503 moving upwards. The electrode 501 connects to the piston 503 through a hinge joint 508. The hinge joint 508 allows uniaxial movement of the electrodes 501. Cuffs 507 help to support the actuator 505 when worn on the wrist.

An actuator similar to actuator 505 may be secured to other areas of the body besides the wrist area. When secured to areas other than the wrist, different arrangements, other than cuffs, may be used in order to secure the actuator portion to that area. In an embodiment, an actuator 505 is secured to a leg. In an embodiment, an actuator 505 is secured to an arm. In an embodiment, an actuator 505 is secured to a neck. In an embodiment, an actuator 505 is secured to a waist. In an embodiment, an actuator is secured to a head. In an embodiment, an actuator is secured to a chest.

Figure 6:
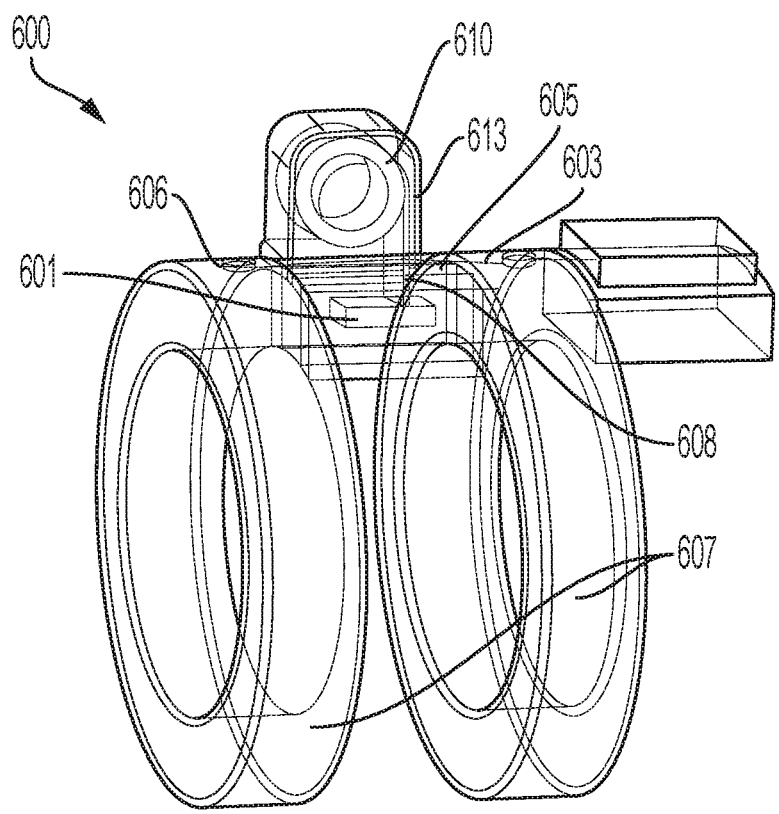
FIG. 6 is a diagram of a pressure adaptive sensing system.

Now referring to FIG. 6, shown is an embodiment of an actuator 605 for the sensing system 600 that uses a constant force spring 610. A constant force spring 610 is mounted on a two-ring cuff 607 that is connected through the housing 606 of the actuator 605 and holds the force spring 603 in place. Each electrode 601 is attached to the end of a force spring 610. A portion of the force spring 610 is guided through the walls of an enclosure that surrounds the force spring 610 and is operably attached to the electrode 601. In FIG. 6, the electrode 601 is attached to the constant force spring 610 by a 3D printed hinge 608. In an embodiment, the electrode is attached to a force spring using a hinge.

When a specific current is applied to the muscle wire 603 it contracts. The contraction of the muscle wire 603 unrolls the constant force spring 610. The unrolling of the constant force spring 610 brings the electrode 601 into contact with the skin. The muscle wire 603 loops through the constant force spring layer. When current is applied to the muscle wire 603, it contracts 5% of its length and unrolls the constant force spring 610. Unrolling of the constant force spring 610 guides a portion of the constant force spring 610 through the enclosure wall 613. The portion of the constant force spring 610 that is through the enclosure wall 613 brings the electrode 601 into contact with the skin. In an embodiment, the muscle wire contracts 1 to 5% of its length. In an embodiment, the muscle wire contracts 1 to 10% of its length. In an embodiment, the muscle wire contracts a quarter of its length. In an embodiment, the muscle wire contracts more than quarter of its length.

The actuator 605 is supported by two cuffs 607. Through the use of the two cuffs 607, the housing 606 is located on the wrist. In an embodiment, a layer of memory foam is placed inside the cuffs 607. The memory foam assists in adapting the cuffs 607 to fit different wrist sizes. In an embodiment, electrical components may be stored in an enclosure within the housing. In the embodiments discussed above, when components are used to operatively attach an actuator to a person, memory foam can be placed within an interior of the cuffs or other attachment mechanism in order to securely fit the device to the body part.

An actuator similar to actuator 605 may be secured to other areas of the body besides the wrist area. When secured to areas other than the wrist, different arrangements, other than cuffs, may be used in order to secure the actuator portion to that area. In an embodiment, an actuator 605 is secured to a leg. In an embodiment, an actuator 605 is secured to an arm. In an embodiment, an actuator 605 is secured to a neck. In an embodiment, an actuator 605 is secured to a waist. In an embodiment, an actuator 605 is secured to a head. In an embodiment, an actuator 605 is secured to a chest.

Figure 7:
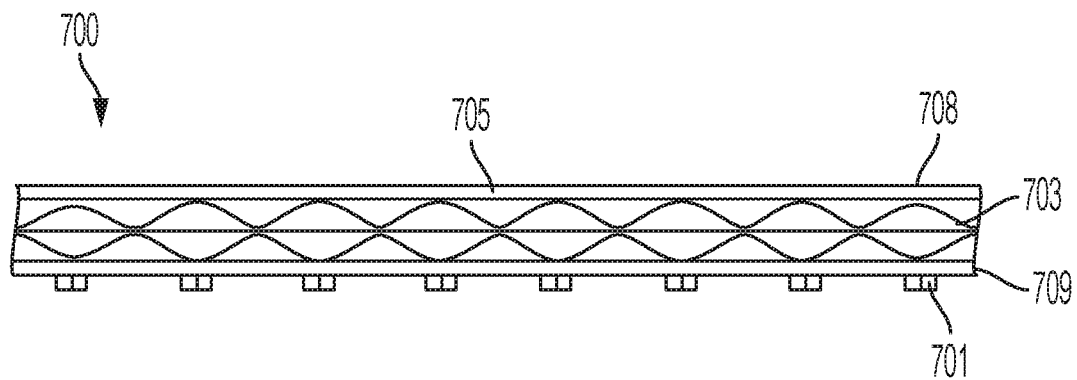
FIG. 7 is a diagram of a pressure adaptive sensing system.

Now referring to FIG. 7, shown is an embodiment of a sensing system 700 that is a pressurized actuator 705 which encircles a part of a user's body and which controls the pressure exerted on the electrodes 701 (which can be transmitting or receiving electrodes). The pressurized actuator 705 comprises an air-bladder 703 connected to an electrical pump (not shown) that pressurizes the actuator 705. The pressurized actuator 705 and its air-bladder 703 are able to provide measurements on pressure when in contact with a body part. Additionally, in an embodiment, the pressurized actuator 705 is able to provide measurements of impedance with respect to the sensing system 700 and the skin.

To optimize a contact profile for the electrode 701, each air-bladder 703 has its own valve. In an embodiment, each valve is electrically activated and is pressurized independently. In an embodiment, each valve is mechanically activated and is pressurized independently. In an embodiment, electrodes 701 attach to a memory foam layer 709 that dampen the forces exerted from the skin onto the electrodes 701. In an embodiment, air-bladder 703 is mechanically pressurized, thereby exerting a compression force onto the electrodes 701. In an embodiment, air-bladder 703 is electrically pressurized via electronic components thereby exerting a compression force onto the electrodes 701. In an embodiment, a rigid plastic outermost layer 708 supports all other layers.

In another embodiment, an electromagnetic or piezoelectric device is used to directly drive positions of transmitting and receiving electrodes. The device comprises a low-mass, high-power actuator to control and hold the position of the electrodes against skin or other materials. These actuators have the benefit of fast response times and may be considered as additional actuators and provide pressure adaptation where arrays of multiple actuators are incorporated.

Figure 8:
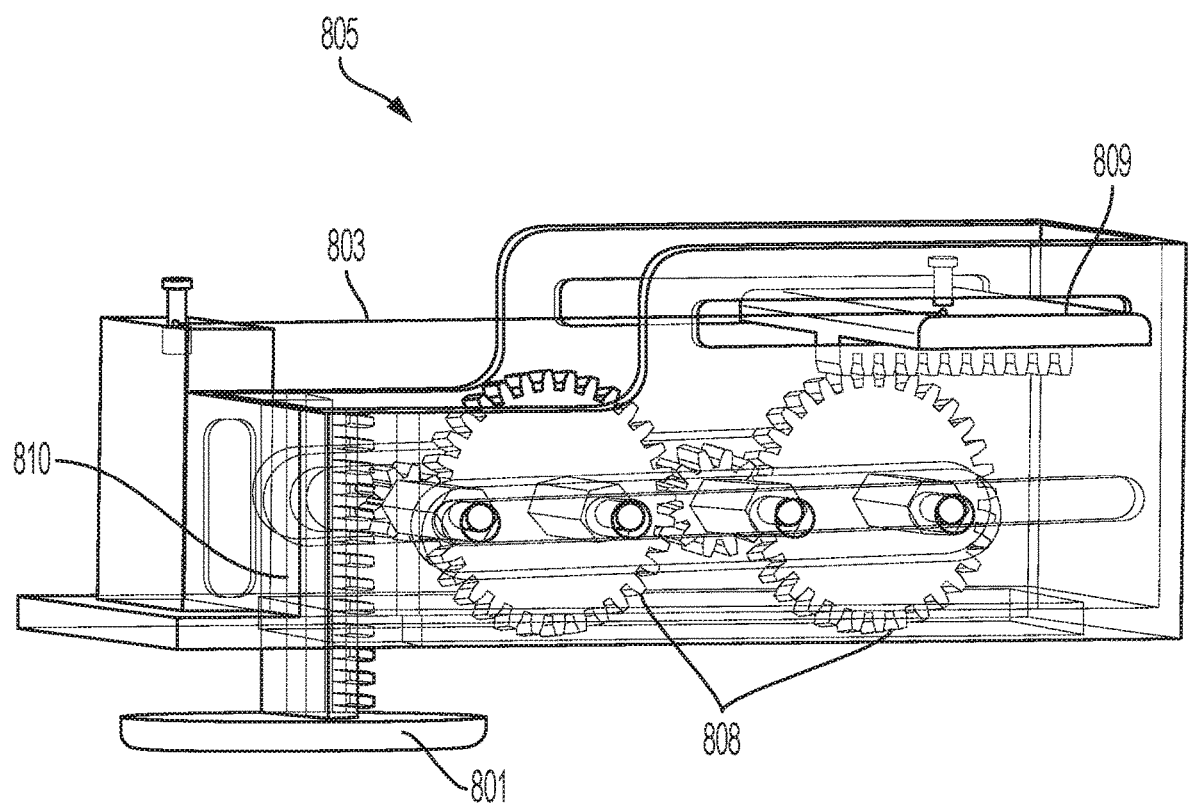
FIG. 8 is a diagram of a pressure adaptive sensing system.

Now referring to FIG. 8, shown is an embodiment of an actuator 805 for a sensing system that uses a combination of a gear-based system and muscle wire. A muscle wire 803 is operatively connected to a gear portion 809 that meshes with gears 808. The gears 808 are operatively connected to a foot 810 that has an electrode 801 located at a distal end.

When a specific current is applied to the muscle wire 803 it contracts. The contraction of the muscle wire 803 activates the gear portion 809. The activation of the muscle wire 803 causes the gear portion 809 to interact with the gears 808. The operation of the gear portion 809 and the gears 808 causes the foot 810 to move thereby moving the electrode 801. Through this mechanism contact with an arm can be adjusted. When current is applied to the muscle wire 803, it contracts 5% of its length and moves the gear portion 809, gears 808 and foot 810. In an embodiment, the muscle wire contracts 1 to 5% of its length. In an embodiment, the muscle wire contracts 1 to 10% of its length. In an embodiment, the muscle wire contracts a quarter of its length. In an embodiment, the muscle wire contracts more than quarter of its length.

The actuator 805 may be supported by cuffs. Through the use of the cuffs, the actuator 805 may be located on the wrist. An actuator similar to actuator 805 may be secured to other areas of the body besides the wrist area. When secured to areas other than the wrist, different arrangements, other than cuffs, may be used in order to secure the actuator portion to that area. In an embodiment, an actuator 805 is secured to a leg. In an embodiment, an actuator 805 is secured to an arm. In an embodiment, an actuator 805 is secured to a neck. In an embodiment, an actuator 805 is secured to a waist. In an embodiment, an actuator 805 is secured to a head. In an embodiment, an actuator 805 is secured to a chest.

Figure 9:
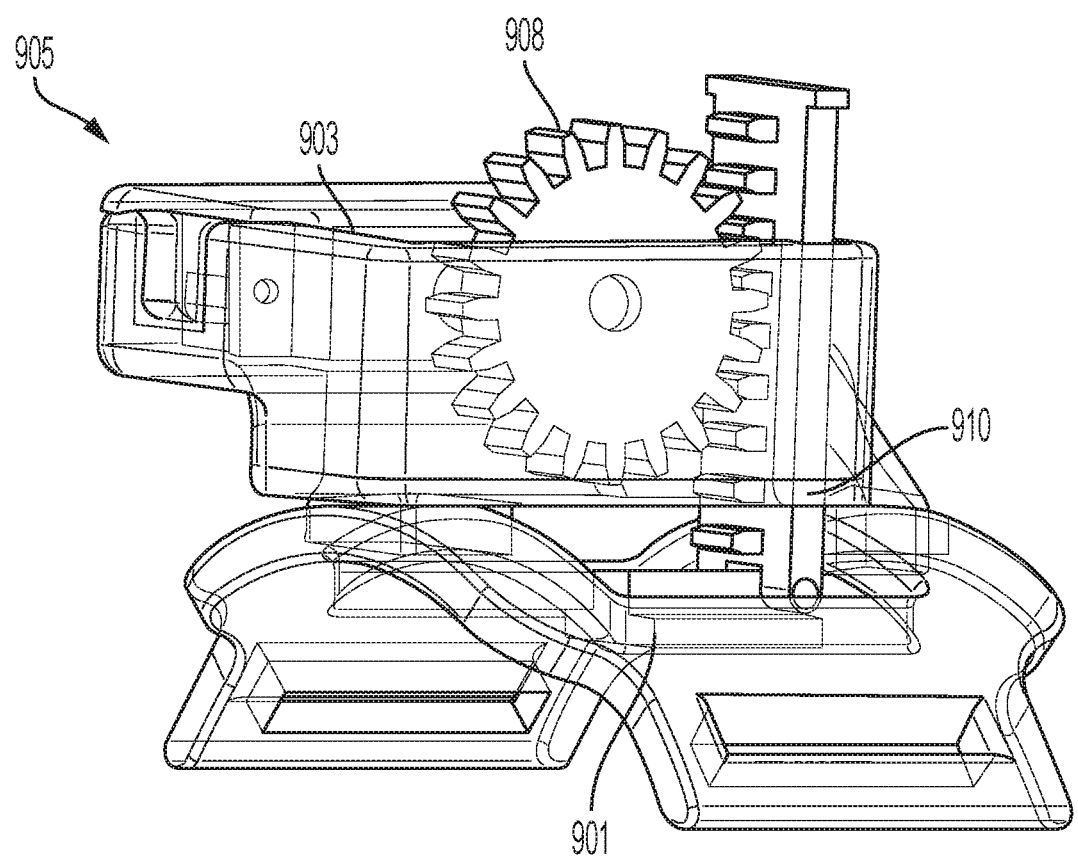
FIG. 9 is a diagram of a pressure adaptive sensing system.

Now referring to FIG. 9, shown is an embodiment of an actuator 905 for a sensing system that uses a servo and rack and pinion mechanism. A servomechanism 903 is operably connected to the gear 908 which, in turn, is connected to the foot 910. Connected to the foot is an electrode 901.

Operation of the servomechanism 903 causes the electrode 901 to either increase or decrease the amount of contact that the electrode 901 has with a body part. Activation of the servomechanism 903 can be controlled via the overall system and can be activated prior and in response to the determination of the amount of contact the electrode 901 has with the body part, thereby optimizing the ability of the system to determine measurements of parts of the body.

The actuator 905 may be supported by cuffs. Through the use of the cuffs, the actuator 905 may be located on the wrist. An actuator similar to actuator 905 may be secured to other areas of the body besides the wrist area. When secured to areas other than the wrist, different arrangements, other than cuffs, may be used in order to secure the actuator portion to that area. In an embodiment, an actuator 905 is secured to a leg. In an embodiment, an actuator 905 is secured to an arm. In an embodiment, an actuator 905 is secured to a neck. In an embodiment, an actuator 905 is secured to a waist. In an embodiment, an actuator 905 is secured to a head. In an embodiment, an actuator 905 is secured to a chest.

With respect to the pressure adaptive systems discussed above, as the entire system is manipulated and moved, additional factors such as g-forces and slippage may come into effect. The actuators will have sufficient ability to compensate for these disturbances across all electrodes. The main chassis is the conduit for absorbing these effects and allowing the electrodes to operate nominally. For example excessive acceleration of the device is negated by, for example, the cuffs (e.g. the two chassis rings), discussed above with respect to FIGS. 4-6 and applicable to actuator systems in FIGS. 8 and 9 as well, as they are firmly and rigidly coupled to the user's wrist, therefore only the mass of each electrode itself is required to have the excess g-force vector compensated for. The cuffs are described as a pair of solid rings around the wrist, however the rings may be applied to other parts of the body as well. Furthermore, each cuff may be formed of multiple parts, or one cuff may be solid while the other cuff is formed of multiple parts. Applicants of this device can also be extended to a similar construction around the human chest (for a chest cavity scan for example), or through a connection of individual units (i.e. not a rigid ring and instead concatenated chains of ring segments). Formations of rings created with multiple parts would be effective in cases where the body to be scanned is not round but ellipsoidal or irregular in shape, the chain of discrete electrodes/transducers would flex to follow the surface contours of the skin/material. In an embodiment, an entire suit is formed of multiple connected actuators that are able to dynamically adapt to the movements of a user. In an embodiment, wearables for sections of the body are formed of multiple connected actuators.

While wearables used with various body parts are discussed above, principles discussed above with respect to the various embodiments may be used by one of ordinary skill in view of this disclosure to further implement the sensor system discussed above into other wearables that would benefit from establishing contact.

In an embodiment, the pressure adaptive sensor system is implemented in a wearable placed on the ankle. In an embodiment, the pressure adaptive sensor system is implemented in a wearable placed on the arm. In an embodiment, the pressure adaptive sensor system is implemented in a sensing device placed on the chest. In an embodiment, the pressure adaptive sensor system is implemented in a sensing device applied to a breast. In an embodiment, the pressure adaptive sensor system is implemented in a wearable placed on the leg. In an embodiment, the pressure adaptive sensor system is implemented in a wearable placed on the head. In an embodiment, the pressure adaptive sensor system is implemented in a wearable placed on the neck. In an embodiment, the pressure adaptive sensor system is implemented in a wearable placed on the waist. In an embodiment, the pressure adaptive sensor system is implemented in a wearable placed on the hand. In an embodiment, the pressure adaptive sensor system is implemented in a wearable placed on the foot.

Figure 10:
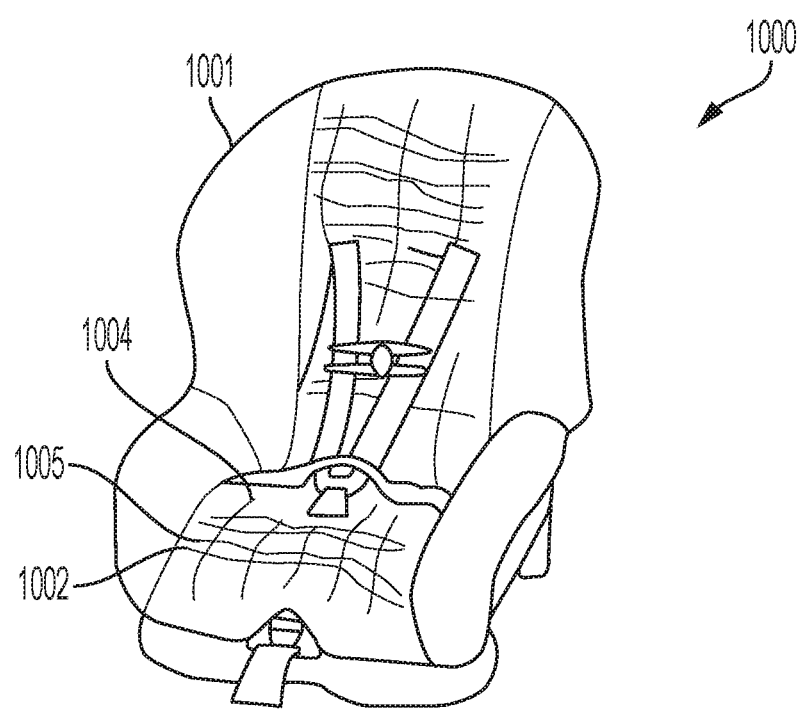
FIG. 10 shows a car seat having a pressure adaptive sensing system.

While wearables are generally discussed above, the pressure adaptive sensing system can also be implemented in other devices and objects. Referring to FIG. 10, shown is a simple diagram of an implementation of the pressure adaptive sensor system 1000 in a car seat 1001. The car seat 1001 has embedded therein a plurality of transmitting antennas 1002 and receiving antennas 1004 formed as a grid of conductors. The transmitting antennas 1002 are operably connected to a signal generator (not shown). A plurality of frequency orthogonal signals are transmitted on each of the transmitting antennas 1002. When a child is present within the car seat 1001, the position and location of the child is determined based on the measured signals received by the receiving antennas 1004.

When detecting the presence of a child within the car seat 1001, the position of the child within the seat can be determined. The determined position of the child within the car seat 1001 can then be used in order to provide feedback to pressure actuators 1005 located within the car seat 1001. The pressure actuators 1005 may run adjacent to the transmitting antennas 1002 and the receiving antennas 1004. The pressure actuators 1005 shown in FIG. 10 are formed from Nitinol®. By applying charge to the pressure actuators 1005, the physical properties of the pressure actuators 305 alter. This results in the overall pressure that is applied to the child in the car seat 1001 additionally alters. This can be used to provide additional comfort to the child in the car seat 1001.

In an embodiment, the pressure actuators are formed as a separate layer of the car seat. In an embodiment, the pressure actuators are formed as a hydraulic system. In an embodiment, the pressure actuators are formed as a pneumatic system. In an embodiment, the pressure actuators are formed as multiple layers of the car seat. In an embodiment, the pressure actuators are located throughout the car seat.

In an embodiment, the pressure adaptive sensor system is placed in furniture. In an embodiment, the pressure adaptive sensor system is placed in car seats. In an embodiment, the pressure adaptive sensor system is placed in plane seats. In an embodiment, the pressure adaptive sensor system is placed in clothing. In an embodiment, the pressure adaptive sensor system is placed in theater seats.

The applications discussed above may employ Electrical Impedance Tomography (EIT) based measurement schemes; however, it is not constrained to such and is equally applicable to ultrasound transducers or modulated-wavelength light based transducers, for example. Typical EIT/Ultrasound systems employ an array of sensor transducers. Each has its own independent characteristic behaviour and is also a function of its location and contact with the skin/material. These systems typically require a complex calibration scheme that compensates algorithmically for differences in each transducer. Our aim is to extend this calibration to include runtime active actuation/adaptation of the physical transducer, using a closed loop feedback controller, with a setpoint goal of maintaining a constant pressure and area of skin contact for each independent electrode.

Another embodiment of the adaptive pressure systems may be a robotic gripper such as in a grip system for robotics. In this application the electrodes/transducers are formed as the grip fingers for the robot and enable the grip pressure to be controlled uniquely through each independent unit. The feedback of impedance and pressure/strain and/or sound coupling (in the case of ultrasound) are used to adjust the grip force and maintain control. In an embodiment, robotic systems are used for medical applications. In an embodiment, robotic systems are used for mining. In an embodiment, robotic systems are used for industrial applications.

An aspect of this disclosure is a sensing system. The sensing system comprises a plurality of transmitting antennas operably connected to a signal generator, the signal generator adapted to transmit a plurality of frequency orthogonal signals on each one of the plurality of transmitting antennas; a plurality of receiving antennas operably connected to a processor, the plurality of receiving antennas adapted to receive at least one of the plurality of frequency orthogonal signals transmitted by the plurality of transmitting antennas; a processor adapted to process measurements of the plurality of frequency orthogonal signals received in order to determine information regarding a body part, wherein at least one received plurality of frequency orthogonal signals is processed to determine a measurement that provides an indication of pressure on the body part; and a pressure actuator adapted to modify contact with the body part based on the indication of pressure on the body part.

Another aspect of the present invention is a pressure adaptive sensing system. The pressure adaptive sensing system comprises at least one transmitting antenna adapted to transmit a signal; at least one receiving antenna adapted to receive a signal transmitted from the at least one transmitting antenna, wherein a measurement is taken of the signal received at the at least one receiving antenna, wherein the measurement provides an indication of pressure on a body part; and a pressure actuator adapted to modify contact of one of the at least one transmitting antenna and the at least one receiving antenna based on the indication of pressure on the body part determined from the measurement.

While the invention has been particularly shown and described with reference to a preferred embodiment thereof, it will be understood by those skilled in the art that various changes in form and details may be made therein without departing from the spirit and scope of the invention.

The invention claimed is:

1. A sensing system comprising:
a plurality of transmitting antennas operably connected to a signal generator, the signal generator adapted to transmit a plurality of frequency orthogonal signals on each one of the plurality of transmitting antennas;
a plurality of receiving antennas operably connected to a processor, the plurality of receiving antennas adapted to receive at least one of the plurality of frequency orthogonal signals transmitted by the plurality of transmitting antennas;
a processor adapted to process measurements of the plurality of frequency orthogonal signals received in order to determine information regarding a body part, wherein at least one received plurality of frequency orthogonal signals is processed to determine a measurement that provides an indication of pressure on the body part; and
a pressure actuator adapted to modify contact with the body part based on the indication of pressure on the body part.

2. The sensing system of claim 1, wherein the sensing system is part of a wearable adapted to be placed on a wrist.

3. The sensing system of claim 1, wherein the measurement that provides an indication of pressure on the body part is a measurement of impedance.

4. The sensing system of claim 1, wherein the measurement that provides an indication of pressure on the body part is a measurement of voltage taken.

5. The sensing system of claim 1, wherein the pressure actuator comprises a material that changes physical properties using electric charge.

6. The sensing system of claim 1, wherein the pressure actuator comprises components formed from Nitinol.

7. The sensing system of claim 1, wherein the pressure actuator comprises hydraulically activated portions.

8. The sensing system of claim 1, wherein the pressure actuator comprises pneumatically activated portions.

9. The sensing system of claim 1, wherein contact with the body part is modified so as to match a predetermined contact profile.

* * * * *